(12) United States Patent
Protopsaltis

(10) Patent No.: US 8,105,328 B2
(45) Date of Patent: Jan. 31, 2012

(54) MULTIPLE IMPLANT DISPENSING DRIVER

(75) Inventor: Dimitri Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 863 days.

(21) Appl. No.: 11/701,135

(22) Filed: Feb. 1, 2007

(65) Prior Publication Data

US 2008/0255576 A1    Oct. 16, 2008

(51) Int. Cl.
*A61B 17/70* (2006.01)
(52) U.S. Cl. .................. 606/86 A; 606/104; 606/99
(58) Field of Classification Search ............ 606/86 R, 606/86 A, 90, 99, 100, 104, 270, 279, 300–331; 81/456–458, 177.4, 13, 57.37
See application file for complete search history.

(56) References Cited

U.S. PATENT DOCUMENTS

| | | | |
|---|---|---|---|
| 1,537,929 A | | 5/1925 | Henry |
| 2,247,500 A | * | 7/1941 | Hutchison, Jr. ............. 81/125 |
| 4,811,647 A | | 3/1989 | Lindamood |
| 4,958,873 A | | 9/1990 | Akagawa |
| 4,963,144 A | | 10/1990 | Huene |
| 5,352,231 A | | 10/1994 | Brumfield et al. |
| 5,437,211 A | | 8/1995 | Wolfe |
| 5,445,641 A | | 8/1995 | Frigg et al. |
| 5,590,574 A | * | 1/1997 | Lide ............. 81/124.1 |
| 5,649,931 A | | 7/1997 | Bryant et al. |
| 5,735,854 A | * | 4/1998 | Caron et al. ............. 606/916 |
| 5,791,207 A | * | 8/1998 | Ahdoot ............. 81/57.37 |
| 5,941,885 A | | 8/1999 | Jackson |
| 6,112,944 A | | 9/2000 | Van Hoorn et al. |
| 6,129,730 A | | 10/2000 | Bono et al. |
| 6,132,435 A | | 10/2000 | Young |
| 6,224,596 B1 | | 5/2001 | Jackson |
| 6,273,893 B1 | | 8/2001 | McAllen, III et al. |
| 6,283,973 B1 | | 9/2001 | Hubbard et al. |
| 6,328,746 B1 | | 12/2001 | Gambale |
| 6,634,261 B1 | | 10/2003 | Griffin |
| 6,974,466 B2 | | 12/2005 | Ahmed et al. |
| 7,147,641 B2 | * | 12/2006 | Chen ............. 606/104 |
| 7,240,588 B1 | | 7/2007 | Rinner |
| 7,451,893 B2 | | 11/2008 | Martin |
| 2002/0099386 A1 | | 7/2002 | Beger et al. |
| 2004/0243139 A1 | * | 12/2004 | Lewis et al. ............. 606/104 |
| 2005/0149031 A1 | * | 7/2005 | Ciccone et al. ............. 606/73 |
| 2005/0203530 A1 | | 9/2005 | Oribe et al. |
| 2006/0027592 A1 | | 2/2006 | Flamingo et al. |
| 2007/0088363 A1 | | 4/2007 | Rezach |
| 2007/0276403 A1 | | 11/2007 | Franks et al. |

FOREIGN PATENT DOCUMENTS

| | | |
|---|---|---|
| DE | 298 16 215 U1 | 11/1998 |
| FR | 668 187 | 10/1929 |
| GB | 2 355 505 A | 4/2001 |

* cited by examiner

*Primary Examiner* — Eduardo C Robert
*Assistant Examiner* — Steven Cotroneo

(57) ABSTRACT

Instruments and methods are provided for delivering multiple implants to multiple implant locations in a patient without requiring a second implant to be loaded onto or engaged to the delivery instrument after delivery of a first implant. The implants can be sequentially engaged using the delivery instrument to the patient or to receptacles of one or more receiving members secured to the patient.

27 Claims, 10 Drawing Sheets

MULTIPLE IMPLANT DISPENSING DRIVER

BACKGROUND

Various types of devices and systems have been used for positioning implants into a patient in surgical procedures. Spinal stabilization systems have employed plating systems, rods, anchors, fusions devices, artificial discs, and other implants along or in the spinal column for rigid, dynamic, and semi-rigid spinal stabilization procedures. Such systems often include multiple implant members that must be engaged for the system to be properly installed. There remains a need for instruments and methods for delivering multiple implants to the implantation location while minimizing the time and complexity associated with handling and securing such implants during surgery.

SUMMARY

Instruments and methods for positioning multiple implants in surgical procedures include an instrument for delivering multiple implants configured to permit sequential securement of the implants in multiple receptacles of one or more receiving members or at multiple locations in the patient. The delivery instruments and methods permit implantation of multiple implants without any requirement for re-loading or re-engaging a second implant to the instrument after delivery of a first implant.

In one form, there is provided a surgical instrument comprising an elongated interior member receivable within an interior passage of an elongated housing member. The interior passage of the housing member generally extends from a proximal end to an opening at a distal end and includes at least one pair of guides disposed therein. The elongated interior member defines a chamber for holding a plurality of implants at its proximal end, the chamber communicating with at least one pair of positionable implant engaging arms at its distal end. The implant engaging arms include an implant gripping portion structured to engage with one of the plurality of implants. The elongated interior member is moveable within the elongated housing member between a plurality of positions including a loading position and a delivery position. When the interior member is at the loading position, the guides direct the positionable implant engaging arms away from one another to create a pathway for the one implant of the plurality of implants to move from the chamber to the implant gripping portion. The guides direct the implant engaging arms toward each other to engage the implant when the interior member is at the delivery position.

In another form, a surgical instrument for delivering multiple implants to an implantation location is provided. The instrument includes an elongated housing member extending along a longitudinal axis from a transverse operator handle at a proximal end to an opening at a distal end. The housing member defines an internal bore extending axially along the longitudinal axis from the transverse operator handle to the opening. The internal bore includes a pair of guide pins disposed transversely to the longitudinal axis and proximally to the opening. Further included is a dispensing member defining an interior magazine area structured to hold a plurality of implants at its proximal end and a pair of flexible implant engaging arms defining an implant gripping portion at its distal end. Two implant retaining members are included and are pivotally coupled to the housing member adjacent the opening at the distal end of the housing member. The dispensing member is longitudinally translatable within the internal bore of the housing member such that when the dispensing member is moved toward the opening the guide pins stop translational movement at a first position where the implant engaging arms are positioned to engage a first implant with the implant gripping portion. When the dispensing member is moved away from the opening, the guide pins stop translational movement at a second position where the implant engaging arms are spaced apart to release the first implant and form a passageway. A second implant from the magazine is moveable along the passageway toward the implant gripping portion to be engaged by the implant engaging arms. When the implant moves toward the implant gripping portion, the retaining members are biased toward the opening of the housing member to prevent the implant from exiting through the opening of the housing member before being engaged by the implant engaging arms.

In yet another form, there is provided a surgical system including an implantable receiving member including at least one receptacle. The surgical system further includes an instrument including a proximal handle member; a magazine member defining an implant magazine and a distal implant driver; a housing member coupled with the handle member and extending longitudinally about the magazine member with the magazine member being moveable therein; and a pair of implant retaining members at a distal end of the housing member. A plurality of implants is included and is moveably positioned in the implant magazine. As the magazine member is translated in a first direction the implant driver is structured to receive an implant while the retaining members are structured to retain the implant at the implant driver. The implant driver is further structured to tighten about the implant as the magazine member is translated in a second direction. At least one of the implants is engageable with the receiving member when delivered from the implant driver.

Related features, aspects, embodiments, objects and advantages of the present invention will be apparent from the following description.

DESCRIPTION OF THE ILLUSTRATED EMBODIMENTS

Figure 1:
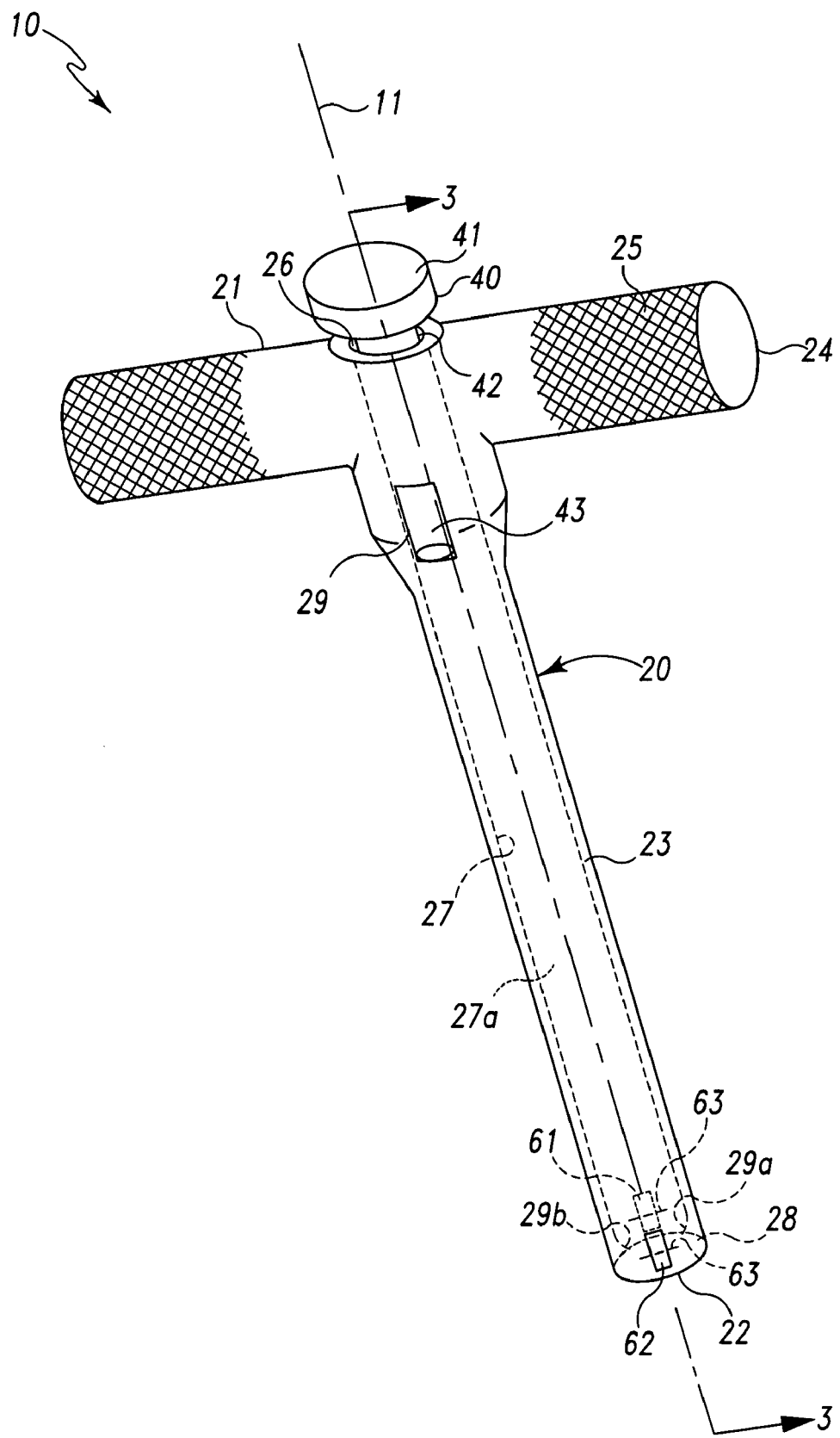
FIG. 1 is a perspective view of one embodiment of a delivery instrument with some features being shown in phantom.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Positioning of multiple implants during a surgical procedure is facilitated by an implant delivery instrument that includes an implant driver disposed within a housing member. The implant driver includes a magazine for holding a plurality of implants and an implant gripping portion in communication with the magazine to receive an implant therefrom. The implant driver is moveable within the housing member to facilitate loading of an implant from the magazine to the implant gripping portion while in one position and gripping of an implant to facilitate insertion to a receiving member while in an alternative position.

Referring now to FIG. 1 there is illustrated in perspective view, with some features being shown in phantom, one embodiment of an implant delivery instrument 10. Instrument 10 includes a housing member 20 including a stem portion 23 extending along longitudinal axis 11 from a proximal end 21 to a distal end 22. An operator handle in the form of T-handle 24 is included at proximal end 21 and includes knurling 25 to assist in handling by a human operator. In alternative embodiments not illustrated, T-handle 24 may include one or more alternative grip improving features, like for example a rubber coating or ergonomic handgrips, or in one embodiment, may be free from any grip improving features. T-handle 24 may be coupled with stem 23 in any manner which provides rotation of instrument 10 when T-handle 24 is rotated. In an embodiment not shown, T-handle 24 includes ratcheting to increase the speed with which instrument 10 may be rotated, like for example, when inserting an implant into a receiving member.

Housing member 20 includes an aperture 26 extending through t-handle 24 in communication with an internal bore 27a. Internal bore 27a is formed by internal wall 27 of stem 23 and extends from aperture 26 to opening 28 at distal end 22. Internal wall 27 includes distally tapered sections 29a, 29b adjacent to opening 28 extending partially or entirely about the circumference of internal bore 27a adjacent to opening 28. Internal bore 27a is appropriately sized and structured to receive implant driver 40, as shown in greater detail in FIGS. 2 and 3, in a manner that permits implant driver 40 to move therein between proximal most and distal most positions. Retaining elements 61, 62 are coupled to stem 23 adjacent distal end 22 of housing member 20 with a pin or detent arrangement, which will be further explained herein, so to pivot about a pivot axis the is orthogonal to longitudinal axis 11.

Figure 2:
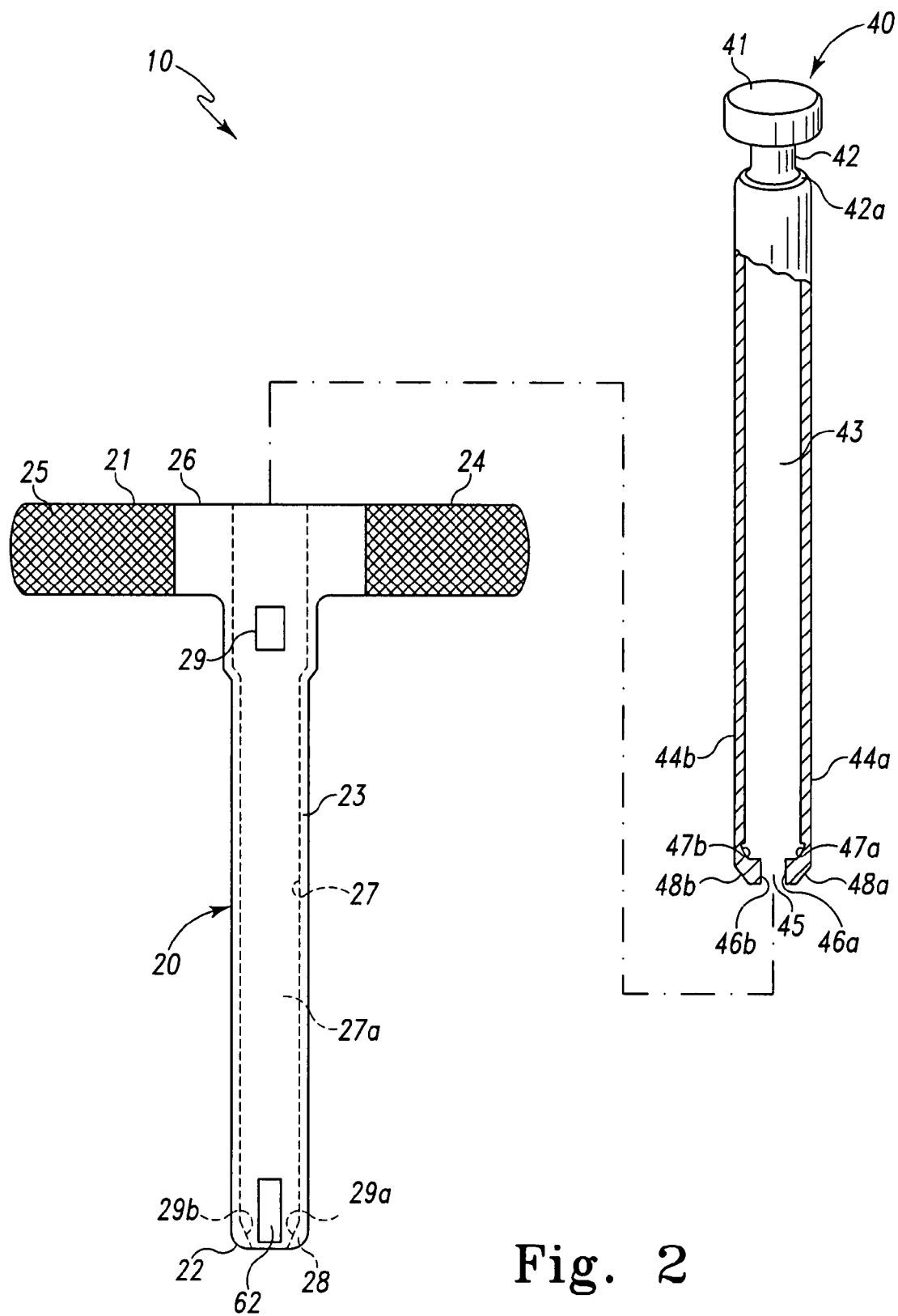
FIG. 2 is an exploded elevational view of the delivery instrument in FIG. 1.

Implant driver 40 includes an operator handle 41 coupled at a proximal end of a shaft 42. Shaft 42 extends from operator handle 41 toward opening 28 and defines a magazine 43 structured to hold a plurality of implants. As illustrated, magazine 43 communicates with a window 29 extending through stem 23 which communicates with internal bore 27a. Window 29 is generally sized and structured to facilitate loading of implants into magazine 43. Referring now to FIG. 2, shaft 42 extends to a proximal collar 42a from which a pair of implant engaging arms 44a, 44b distally extend to define longitudinal magazine 43. At one end of magazine 43 is a distal implant gripping zone 45 disposed between implant engaging surfaces 46a, 46b at the distal ends of respective implant engaging arms 44a, 44b. Furthermore, each of arms 44a, 44b includes inwardly facing grooves 47a, 47b proximally of gripping zone 45, and an external tapered section 48a, 48b along the distal end of arms 44a, 44b. Tapered sections 48a, 48b are structured to engage with tapered sections 29a, 29b of internal wall 27, as shown in FIG. 3.

Figure 3:
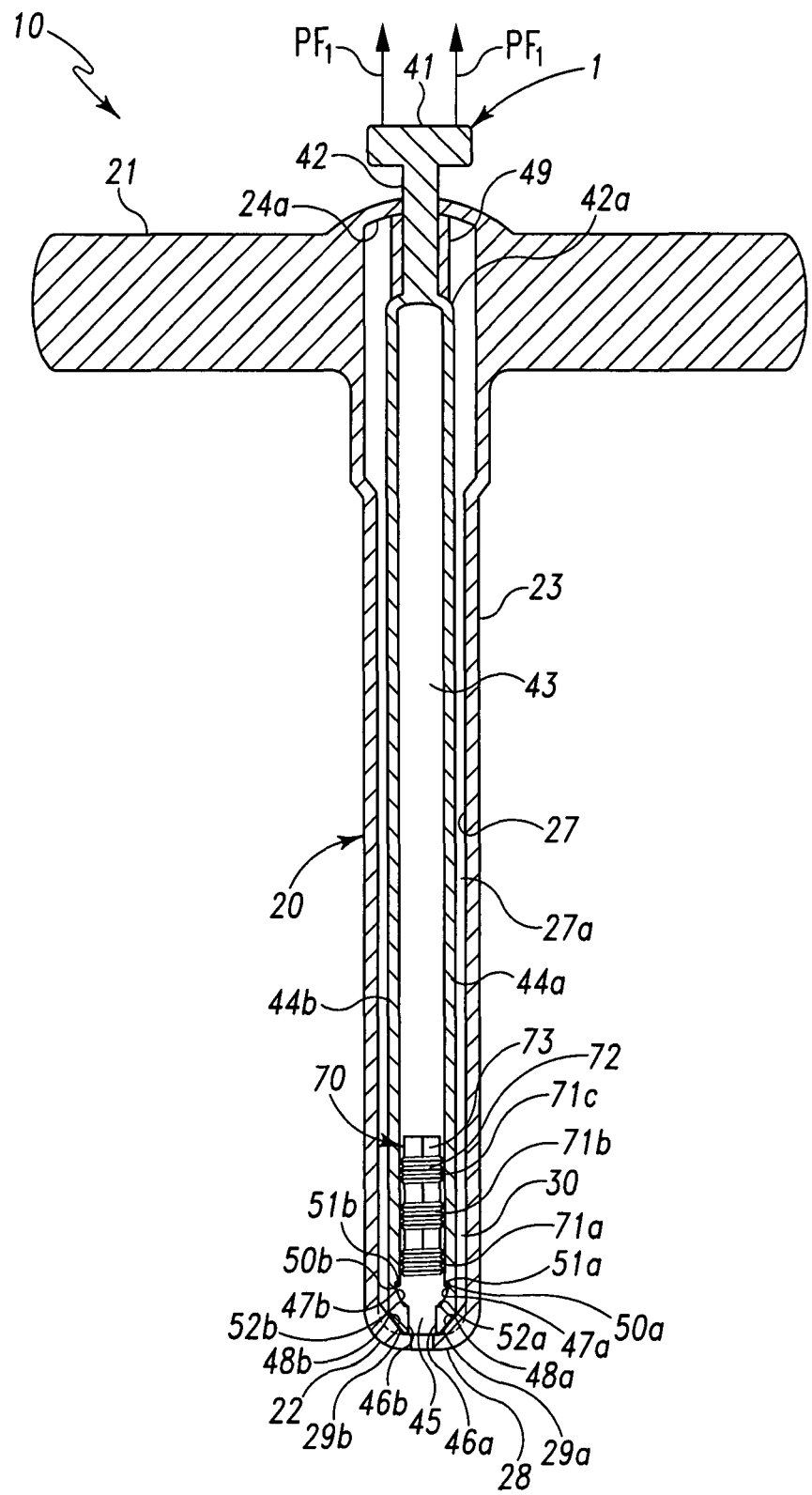
FIG. 3 is a section view of the delivery instrument in FIG. 1 along line 3-3.
Figure 3A:
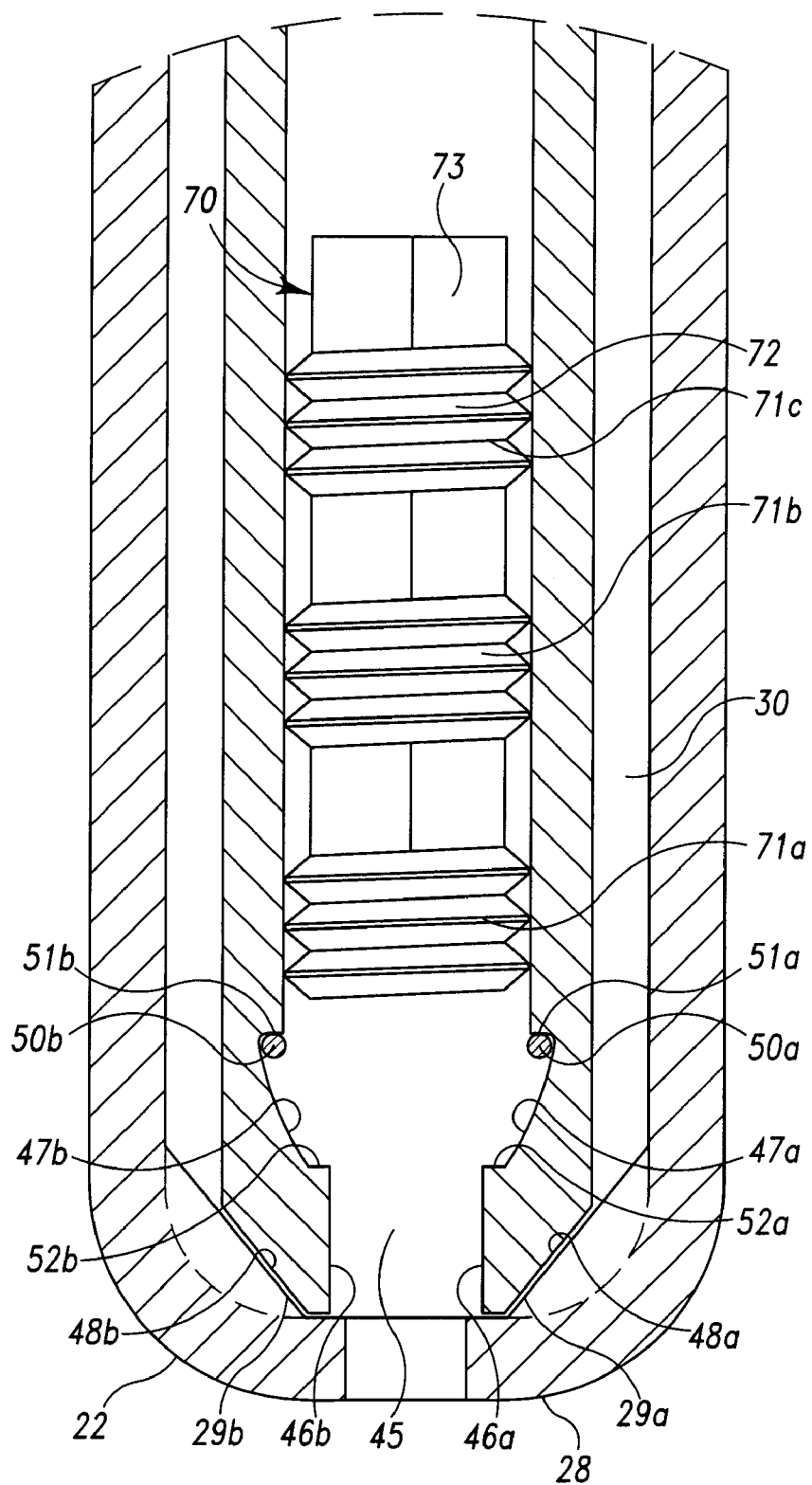
FIG. 3A is an enlarged view of a distal portion of the section view of the delivery instrument shown in FIG. 3.

In FIG. 3, implant driver 40 is situated at its distal most position within internal chamber 27a of housing member 20 such that tapered sections 48a, 48b of each of respective arms 44a, 44b are in a mating relationship with tapered sections 29a, 29b of internal wall 27. In this distal position, tapered sections 29a, 29b force arms 44a, 44b toward, one another to decrease the distance between implant engaging surfaces 46a, 46b at implant gripping zone 45 in a manner to provide gripping of implants 70. Instrument 10 further includes a pair of guide pins 50a, 50b extending orthogonally to longitudinal axis 11 and arms 44a, 44b. Guide pins 50a, 50b engage with the respective adjacent distally and inwardly tapered groove 47a, 47b to direct arms 44a, 44b upon movement of implant driver 40 within housing member 20. When implant driver 40 is at its distal most position, guides pins 50a, 50b contact upper flats 51a, 51b of grooves 47a, 47b to stop the distal movement of implant driver 40, as shown in FIG. 3. Opposite upper flats 51a, 51b are lower flats 52a, 52b which communicate with guide pins 50a, 50b to stop implant driver 40 at its proximal most position.

As illustrated in FIG. 3, instrument 10 includes a compressible biasing element in the form of spring 49 disposed about shaft 42 between collar 42a and internal wall 24a of T-handle 24. As illustrated, spring 49 is in an extended state and forces implant driver 40 toward opening 28 while arms 44a, 44b are directed towards one another at implant gripping zone 45 by guide pins 50a, 50b and distally tapered surfaces 29a, 29b acting on surfaces 48a, 48b. As a user exerts a pulling force $PF_1$ on operator handle 41 to move implant driver 40 to its proximal most position, spring 49 compresses and arms 44a, 44b are guided apart from each other by guide pins 50a, 50b acting on tapered grooves 47a, 47b, and by displacement of the tapered surfaces 48a, 48b proximally away from surfaces 29a, 29b. Proximal movement continues away from opening 28 until lower flats 52a, 52b contact guide pins 50a, 50b to stop implant driver 40 at its proximal most position.

A space 30 remains in internal bore 27a between arms 44a, 44b and internal wall 27 to facilitate separation between arms 44a, 44b when implant driver 40 is at its proximal most position. When implant driver 40 is at its proximal most position, the distance between implant engaging surfaces 46a, 46b at implant gripping zone 45 is increased to facilitate passage of implants 70 from magazine 43 to implant gripping zone 45, as shown in greater detail in FIGS. 4-6. When spring 49 is compressed and a user releases operator handle 41, spring 49 extends toward the extended state and forces implant driver 40 to its distal most position where arms 44a, 44b are forced together to grip implants 70 in gripping zone 45. In alternative embodiments not shown, it is contemplated that instrument 10 may include alternative biasing elements instead of, or in addition to, spring 49. For example, in one embodiment, a pair of springs might be engaged at one end to internal wall 27 near distal end 22 while the other ends are engaged to a more proximal position on arms 44a, 44b, keeping bias on implant driver 40 toward its distal most position.

As illustrated in FIG. 3 and in other drawings, a plurality of implants 70 is provided including a number of externally threaded set screws 71a-c. Set screws 71a-c include a threaded stem portion 72 opposite a hexagonally configured head 73. It is contemplated that head 73 may include any other suitably shaped configuration, including for example, a square or octagonal configuration. In some embodiments, head 73 may be frangible and break away from stem portion 72 upon reaching a threshold of applied torque by instrument 10. Threaded stem portion 72 is structured to be rotatingly engaged with internal threading of a receiving member in a standard manner as would be appreciated by one having ordinary skill in the art. In still other embodiments not shown, implant 70 may be in a form different than set screws 71 a-c. For example, in one embodiment, implant 70 may be structured for engagement directly to bone or soft tissue of the patient.

Figure 4:
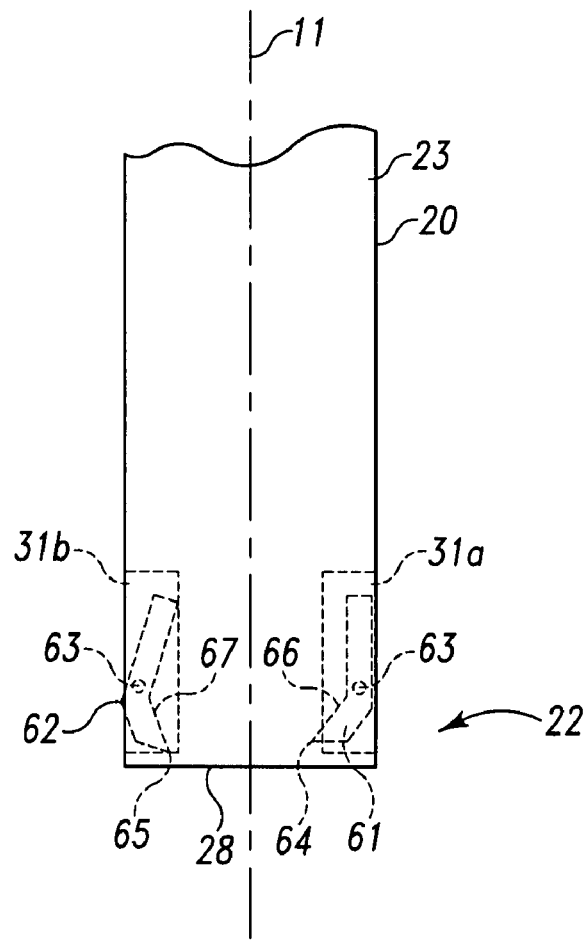
FIG. 4 is an elevation view of the distal portion of the housing member of the delivery instrument in FIG. 1 in partial section to show the retaining elements in first and second positions.

Referring now to FIG. 4, there is shown an enlarged detailed view of a distal portion of housing member 20. Stem portion 23 of housing member 20 includes a pair of opposite and distally and proximally extending recesses 31a, 31b structured to house respective ones of the retaining elements 61, 62. Each of retaining elements 61, 62 is coupled to housing member 20 in the respective recess 31a, 31b about a pivot pin 63 forming a pivot axis. In FIG. 4, the retaining element 61 is shown in a first position, and retaining element 62 is shown in a second position, it being understood that in normal operation retaining elements 61, 62 are both either in the first position or the second position. In one embodiment, a spring element structured to force implant engaging projections 64, 65 toward each other about the respective axis 63 in the first position to engage the distal most implant 70 when implant driver 40 is displaced to its proximal-most position and prevent the distal-most implant from exiting opening 28 until the implant driver 40 is engaged to the distal most implant 70. Retaining elements 61, 62 further include a curved or angled section 66, 67, respectively, structured to join with projections 64, 65 to hold implants 70. Retaining elements 61, 62 are further structured to be movable away from each other at least at inwardly extending projections 64, 65 to a second position, as indicated by retaining element 62. When moved away from each other, projections 64, 65 are spaced sufficiently apart to permit the distal most implant 70 to pass therethrough.

In an alternative embodiment not shown, housing member 20 does not include recesses 31a, 31b to house retaining elements 61, 62. In this embodiment, housing member 20 includes a number of channels formed around the elongate sides of retaining elements 61, 62. The retaining elements remain integrally formed with the housing member through a bridge member at the end thereof opposite from projections 64, 65. The bridge member is structured to provide a living hinge and facilitate movement of retaining elements 61, 62 in a flexibly resilient manner between the first and second positions.

Figure 5:
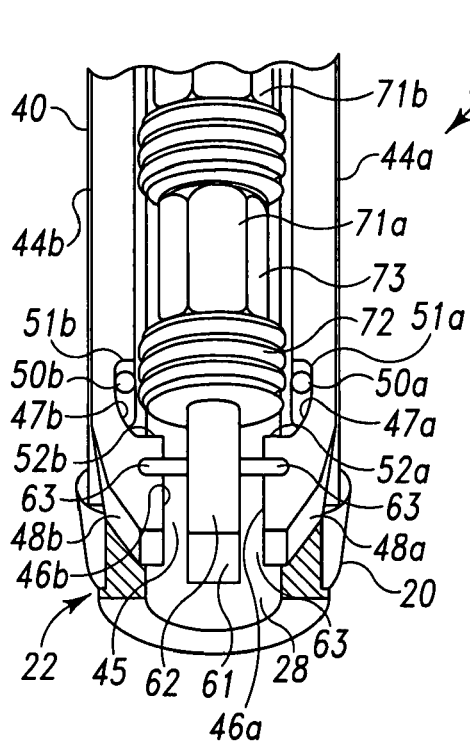
FIG. 5 is an enlarged detailed view in partial section of an implant driver relative to implants and the housing member of the delivery instrument in FIG. 1.
Figure 6:
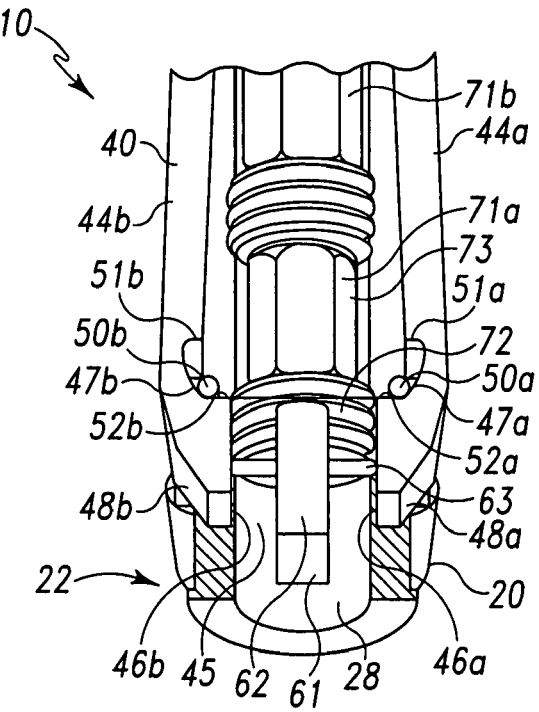
FIG. 6 is an enlarged detailed view in partial section of the implant driver expanded to receive an implant.
Figure 7:
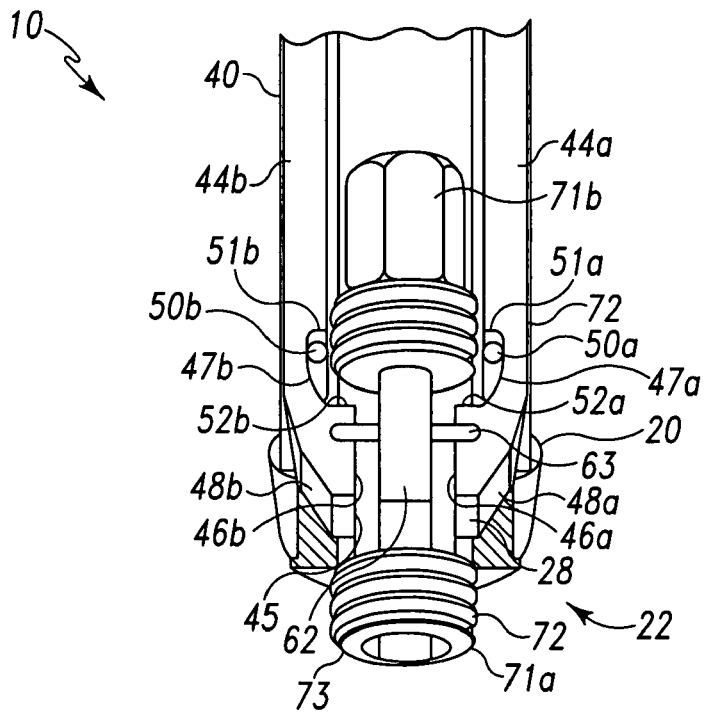
FIG. 7 is an enlarged detailed view in partial section of the implant driver engaging the implant.

In FIGS. 5-7, there is an enlarged detailed view of distal end 22 of instrument 10 including the progression of set screw 71a from magazine 43 to implant gripping zone 45 between implant engaging arms 44a, 44b. Set screw 71a is retained in magazine 43 above implant gripping zone 45 when upper flats 51a, 51b are in contact with guide pins 50a, 50b and implant driver 40 is at its distal most position. When implant driver 40 is moved from its distal most position to its proximal most position, arms 44a, 44b are directed apart by guide pins 50a, 50b acting on tapered surfaces 47a, 47b while lower flats 52a, 52b come into contact with guide pins 50a, 50b. As this occurs, implant gripping zone 45 between implant engaging surfaces 46a, 46b becomes larger and threaded stem 72 of set screw 71a moves into implant gripping zone 45. It should be understood that in the illustrated embodiment, set screw 71a is advanced toward zone 45 by a gravity force. As set screw 71a moves through zone 45, threaded stem 72 contacts curved sections 66, 67 of retaining members 61, 62 to bias projections 64, 65 away from each other so that set screw 71a may pass therebetween. Set screw 71a continues to move toward opening 28 until head 73 is between implant engaging surfaces 46a, 46b at zone 45. At this point, spring 49 forces implant driver 40 toward its distal most position while arms 44a, 44b are guided toward one another by guide pins 50a, 50b and by the mating relationship between tapered sections 48a, 48b with sections 29a, 29b. As arms 44a, 44b come closer, they begin to grip head 73 of set screw 71a with implant engaging surfaces 46a, 46b. While arms 44a, 44b are still moving toward one another, retaining elements 61, 62 provide sufficient resistance so that projections 64, 65 engage a lip or recess extending about set screw 71 to keep it from falling beyond zone 45 until surfaces 46a, 46b can engage it. Once surfaces 46a, 46b fully engage head 73, instrument 10 may be used to insert set screw 71a into a threaded receiving member. After the set screw is threadingly engaged to the receiving member, retaining elements 61, 62 are forced away from one another by the proximally applied force to disengage driver 10 from the engaged set screw.

Figure 8:
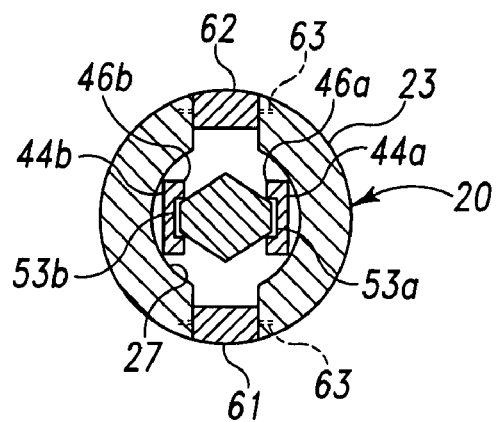
FIG. 8 is a sectional view of the distal end of the delivery instrument in FIG. 1 engaged to an implant.

Further details of implant engaging surfaces 46a, 46b are shown in a cross-sectional view in FIG. 8. Each of implant engaging surfaces 46a, 46b includes a recess 53a, 53b respectively. Recesses 53a, 53b are generally structured to engage with a pair of opposite faces 54a, 54b of hexagonal head 73 of set screws 71a-c. Retaining elements 61, 62 are disposed about opening 28 and oppose each other in a manner generally transverse to implant engaging surfaces 46a, 46b. Projections 64, 65 of retaining members 61, 62 are biased and normally situated between implant engaging surfaces 46a, 46b. In FIG. 8, set screw 71a is engaged by surfaces 46a, 46b and projections 64, 65 are positioned between surfaces 46a, 46b to contact screw 71a as shown in FIG. 7, for example, to maintain it in gripping zone 45 until engaging surfaces 46a, 46b engage set screw 71a.

Figure 9:
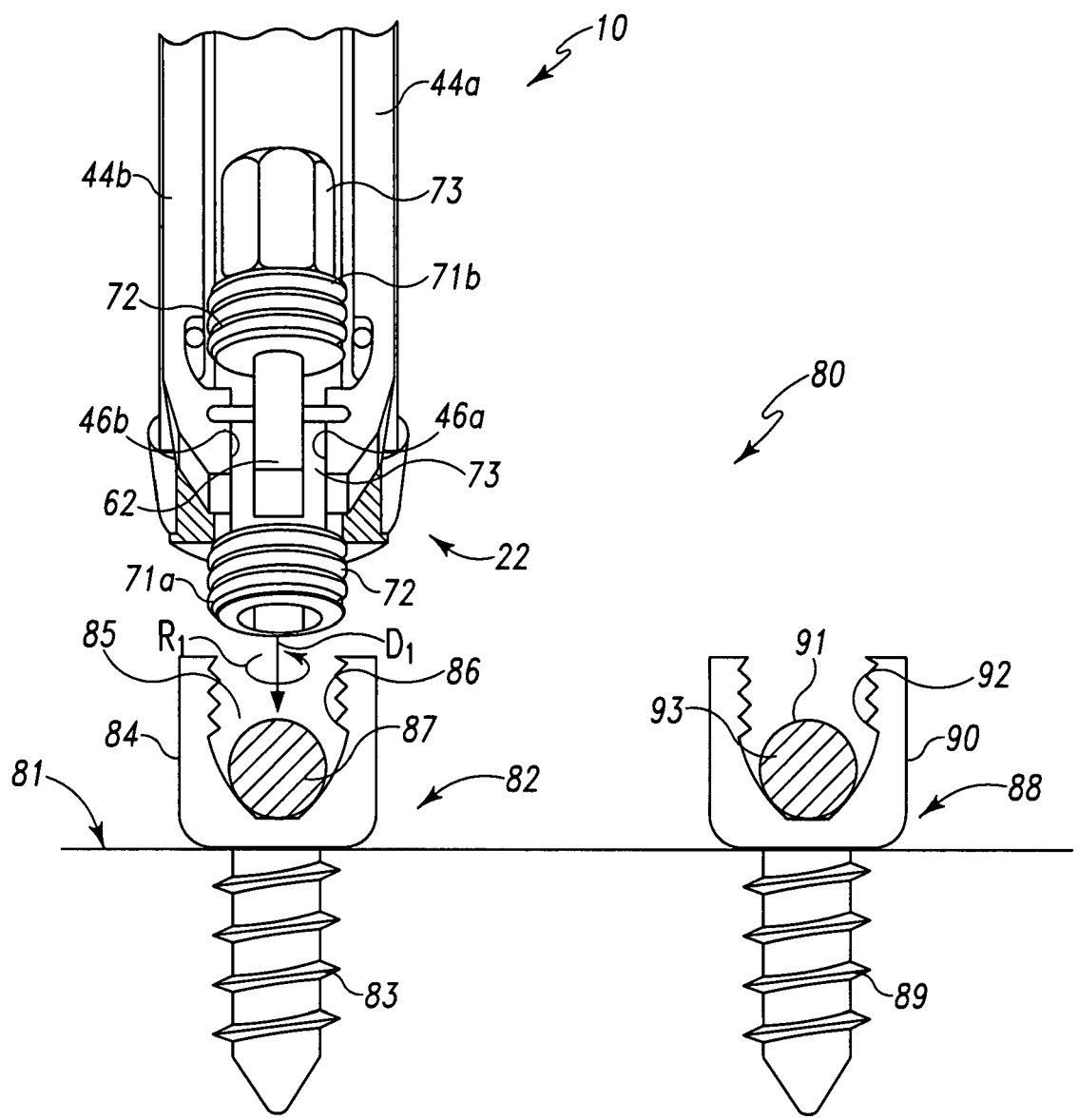
FIG. 9 is an elevation view of the delivery instrument of FIG. 1 relative to a pair of receiving members at a patient surgical site.
Figure 10:
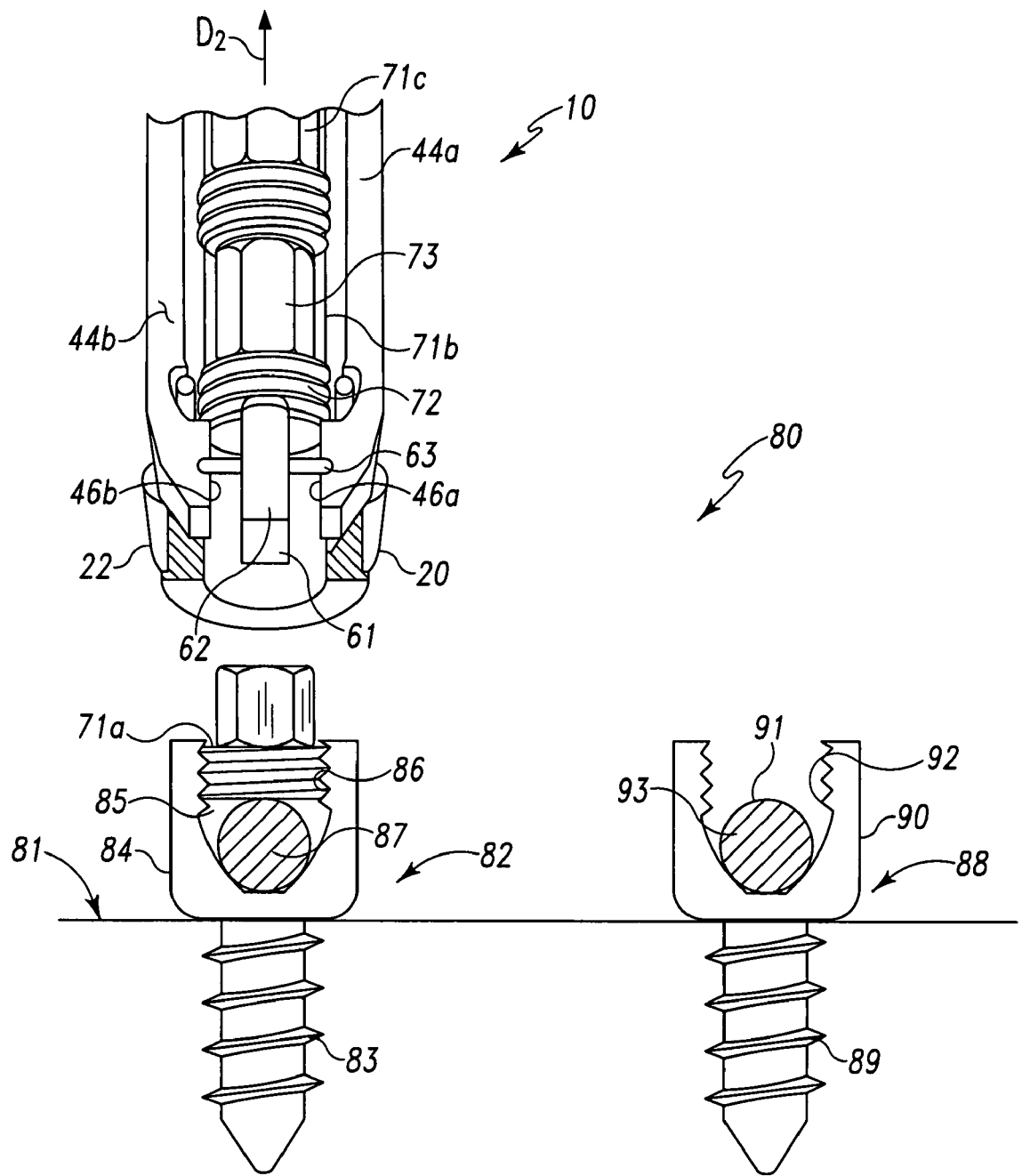
FIG. 10 is the view of FIG. 9 with an implant delivered to a first of the receiving members.
Figure 11:
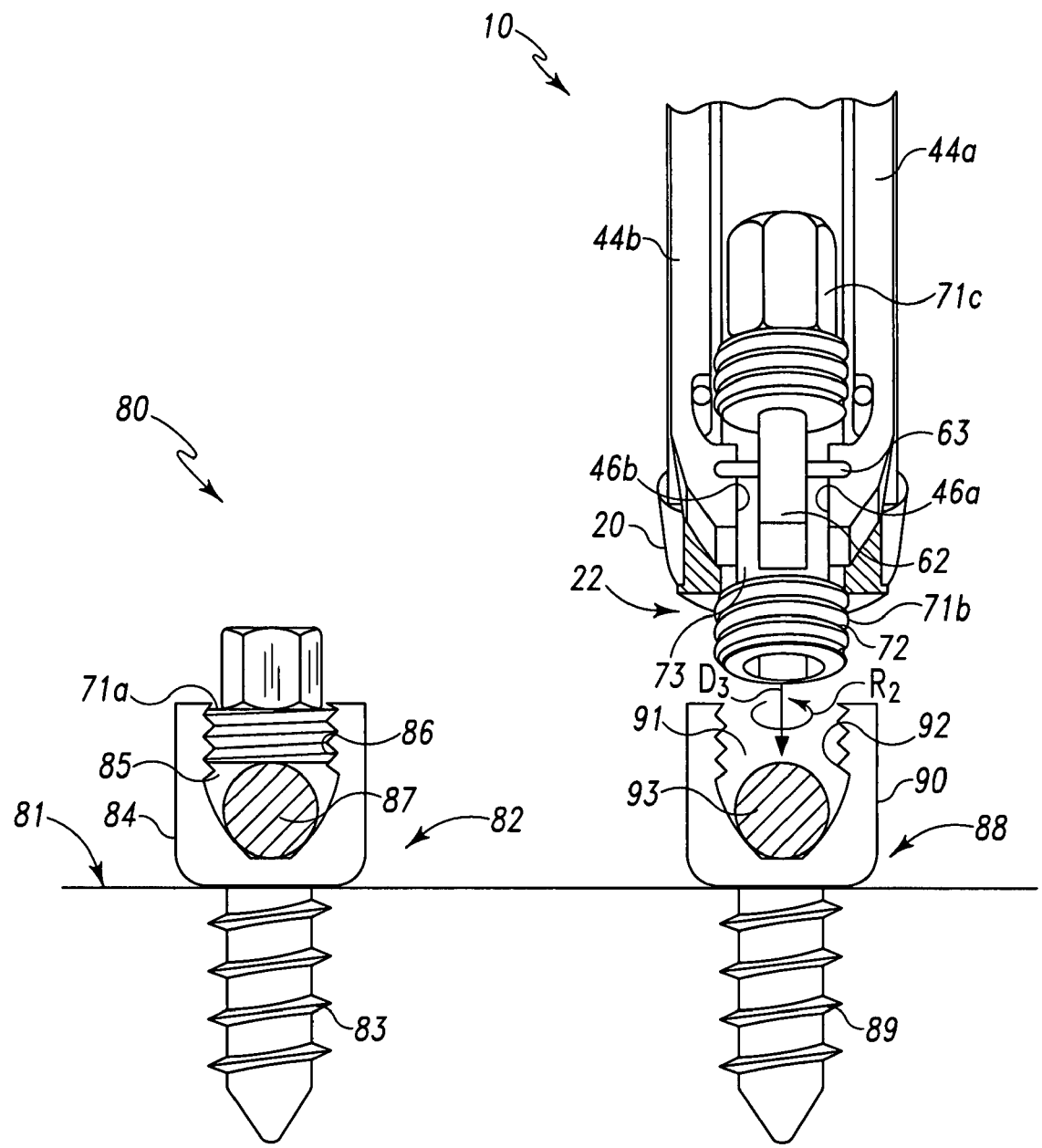
FIG. 11 is the view of FIG. 10 with the delivery instrument positioned relative to a second of the receiving members.

Referring now to FIGS. 9-11 there is shown in elevation view an enlarged detailed view of the distal portion of instrument 10, including the features described herein, relative to a spinal implant system 80. Spinal implant system 80 includes bone screws 82, 88 implanted into one or more vertebral bodies 81. Bone screws 82, 88 each include a longitudinal threaded stem 83, 89, opposite a head portion 84, 90, respectively. Threaded stems 83, 89 are structured to threadingly engage a passageway prepared in one or more bones or bony structures in a standard manner, and can be provided with cutting flutes or other structure for self-tapping and/or self-drilling capabilities. Stems 83, 89 can also be cannulated to receive a guidewire to facilitate placement and may further include fenestrations or other openings for placement of bone growth material.

Head portions 84, 90 each respectively define a rod receiving channel 85, 91 including internal threading 86, 92. It should be understood that bone screws 82, 88 may be, but are not limited to being, a multi-axial, poly-axial, uni-axial, or uni-planar bone screw where stems 83, 89 and head portions 84, 90 are movable relative to one another or are fixed relative to one another. Furthermore, in one form bone screws 82, 88 are made of medical grade stainless steel but in other embodiments may be composed of, but are not limited to, titanium, a titanium alloy or other metallic alloy, and/or a nonmetallic composition. Rods 87, 93 have been placed in each of respective bone screws 82, 88 and are generally structured to provide interconnection with additional components of system 80. Rods 87, 93 may be for example, solid or hollow along some or all of their length and/or may be of homogenous or heterogeneous composition. Additionally, rods 87, 93 can be rigid, or can be flexible or include one or more flexible portions to permit at least limited spinal motion. It should be understood that system 80 and its components have been shown for illustrative purposes only, and that instrument 10 is suitable for use with system 80 including alternative components and with a multitude of alternative surgical systems and devices in addition to or in lieu of system 80.

In FIG. 9, set screw 71a is engaged by surfaces 46a, 46b of implant driver 40 in a manner to facilitate rotational placement into bone screw 82. Distal end 22 of instrument 10 is moved in direction $D_1$ toward bone screw 82 and rotated as designated by directional arrow $R_1$ to threadingly engage set screw 71a with internal threading 86. Instrument 10 is rotated until set screw 71a bears down on elongated rod 87 and elongated rod 87 is securely fastened to bone screw 82. Once set screw 71a is completely engaged therewith, a user may apply pulling force $PF_1$ to operator handle 41 to move implant driver 40 to its proximal most position, according to the description set forth herein in regard to FIGS. 5-7. As surfaces 46a, 46b disengage with head 73 of set screw 71a, instrument 10 may be moved in direction $D_2$ to displace retaining members 61, 62 from engagement with set screw 71a and leave set screw 71a engaged with bone screw 82. In an alternative embodiment where implants 70 include a frangible head position, instrument 10 may be used to deliver implants 70 with or without applying sufficient torque to break off the frangible head portion. If the head portion is broken off, instrument 10 may be used to capture and discard the broken off head from implant system 80. The broken off head is held by surfaces 46a, 46b until released therefrom in accordance with the description set forth herein.

A second set screw 71b, including threaded stem 72 and a hexagonally configured head 73, is then advanced between implant engaging surfaces 46a, 46b according to the description set forth herein in association with FIGS. 5-7. Once set screw 71b is securely engaged between surfaces 46a, 46b, as shown in FIG. 11, instrument 10 is moved in direction $D_3$ and rotated in direction $R_2$ to engage threaded stem 72 of set screw 71b with internal threading 92 of bone screw 88, as described herein in regard to bone screw 82. The process set forth in FIGS. 9-11 can be repeated until the desired number of implants have been delivered or until all implants have been delivered from delivery instrument 10.

Figure 12:
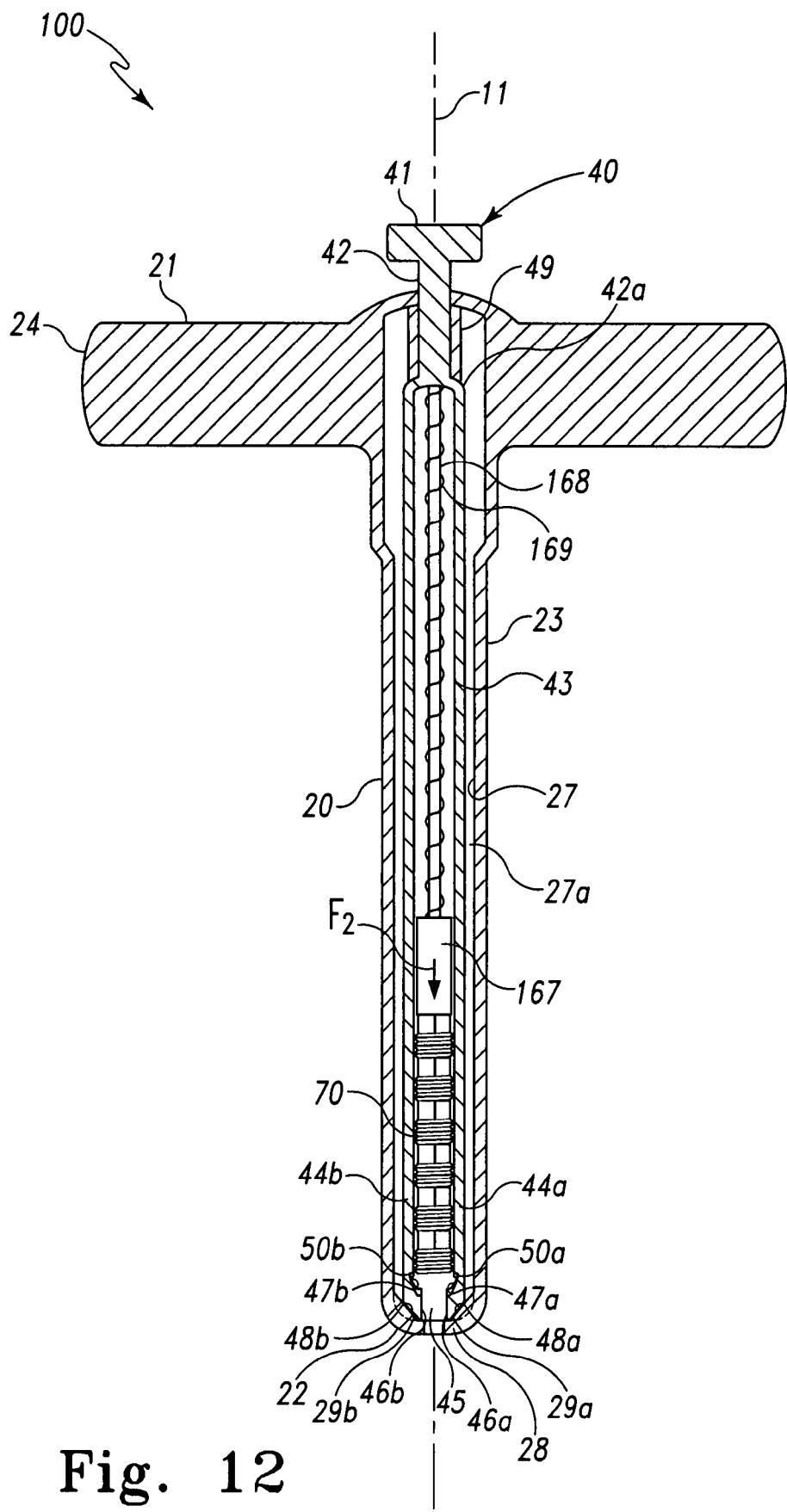
FIG. 12 is a longitudinal section view of an alternative embodiment delivery instrument.

Referring now to FIG. 12 there is shown an alternative embodiment of a delivery instrument 100 in longitudinal sectional view. Instrument 100 generally includes the same features as instrument 10, and like elements are designated with the same reference numeral. Whereas instrument 10 uses the force of gravity to move the plurality of implants 70 toward opening 28, instrument 100 includes a pushing member 167 structured to bear against the proximal most one of the plurality of implants 70 and force them toward opening 28. Pushing member 167 is connected to a telescoping shaft 168 surrounded by a coil spring 169. Telescoping shaft 168 attaches to driver member 40 at collar 42a and is expandable therefrom and contractable thereto along longitudinal axis 11. As pushing member 167 is forced toward collar 42a to create space for loading a plurality of implants 170, telescoping arm 168 contracts while coil spring 169 compresses. Once all of the plurality of implants 70 are loaded in magazine 43, pushing member 167 is biased by compressed coil spring 169 and exerts a force $F_2$ on the plurality of implants 70 pushing them toward opening 28. Force $F_2$ remains constant on the plurality of implants 70 until the last implant has been received in implant gripping zone 45. It should be understood that alternative embodiments for influencing or biasing pushing member 167 toward the plurality of implants 70 are contemplated. For example, instrument 10 may include, but is not limited to including, coil spring 169 by itself without telescoping arm 168 or may include one or more elastic bands connected to pushing member 167 at a first end and to implant engaging arms 44a, 44b adjacent to opening 28 at a second end, creating a pulling force on pushing member 167 toward opening 28.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A surgical instrument comprising:

an elongated interior member extending along a longitudinal axis and defining a chamber for holding a plurality of implants therein, the chamber communicating with at least one pair of positionable implant engaging arms at a distal end of the interior member, the implant engaging arms including an implant gripping portion;

an elongated housing member extending along said longitudinal axis and defining an interior passage extending from a proximal end to an opening at a distal end, the interior passage including at least one pair of guides disposed therein; and wherein the elongated interior member is received within the interior passage of the elongated housing member and is moveable therewithin between a plurality of positions including a loading position wherein the guides contact the positionable implant engaging arms to direct the implant engaging arms away from each other as the elongated interior member is moved along the guides in a first direction along said longitudinal axis relative to the elongated housing member to create a pathway for one of the plurality of implants to move from the chamber to the implant gripping portion and a delivery position wherein the implant engaging arms are directed toward each other as the elongated interior member is moved relative to the guides and the elongated housing member in a second direction along said longitudinal axis opposite the first direction to engage the implant with the implant gripping portion.

2. The surgical instrument of claim 1, wherein the elongated housing member further comprises at least one pair of pivotal retaining elements oppositely disposed about the opening at the distal end of the elongated housing member.

3. The surgical instrument of claim 2, wherein the retaining elements include a first position where distal ends thereof prevent the implant from falling from the implant gripping portion when the elongated interior member is at the loading position and the implant engaging arms are directed away from each other.

4. The surgical instrument of claim 3, wherein the distal ends of the retaining elements are moveable away from each other to permit the implant to disengage from the surgical instrument when released by the implant gripping portion.

5. The surgical instrument of claim 4, further comprising a first tapered region disposed adjacent to the distal end of the elongated interior member and a second tapered region disposed within the interior passage of the elongated housing member adjacent to the opening at the distal end of the housing member, wherein the first tapered region mates with the second tapered region to force the implant engaging arms toward each other when the elongated interior member is at the delivery position.

6. The surgical instrument of claim 5, wherein the implant engaging arms are elongated and extend distally from a proximal collar of the interior member to the implant gripping portion at a distal end of the arms.

7. The surgical instrument of claim 1, further comprising a compressible biasing member adjustably connecting the elongated interior member with the elongated housing member.

8. The surgical instrument of claim 7, further comprising a first tapered region disposed adjacent to the distal end of the elongated interior member and a second tapered region disposed within the interior passage of the elongated housing member adjacent to the opening at the distal end of the elongated housing member, wherein the first tapered region mates with the second tapered region to force the implant engaging arms toward each other when the elongated interior member is at the delivery position.

9. The surgical instrument of claim 7, further comprising an operator handle extending from the proximal end of the elongated interior member and through the proximal end of the elongated housing member and wherein a force applied to the operator handle moves the operator handle away from the housing member to place the interior member in the loading position while compressing the biasing member.

10. The surgical instrument of claim 9, wherein the biasing member biases the elongated interior member to the delivery position and the implant engaging arms include tapered surfaces that mate with at least one of a tapered surface and a guide member to bias the implant engaging arms toward each other.

11. The surgical instrument of claim 7, wherein the elongated housing member further comprises at least one pair of retaining elements oppositely disposed adjacent the opening at the distal end of the elongated housing member.

12. The surgical instrument of claim 11, wherein distal ends of the retaining elements are spaced from one another to prevent the one implant from falling from the implant gripping portion when the elongated interior member is at the loading position and the implant engaging arms are directed away from each other.

13. The surgical instrument of claim 12, wherein the distal ends of the retaining elements are moveable away from each other to release the one implant from the surgical instrument when the implant is released by the implant engaging arms.

14. The surgical instrument of claim 1, wherein the elongated housing member further includes an implant loading window extending therethrough in communication with the chamber of the elongated interior member.

15. The surgical instrument of claim 1, wherein the elongated housing member further includes a T-shaped handle extending from a proximal end of the housing member.

16. The surgical instrument of claim 1, wherein the plurality of implants comprise externally threaded set screws threadingly engageable with an implantable receiving member, the set screws each comprising a proximal head portion and a distal threaded portion.

17. The surgical instrument of claim 16, wherein the implant gripping portion of the implant engaging arms includes a pair of grooves structured to matingly engage with the head portion of the set screw.

18. A surgical instrument for delivering multiple implants to an implantation location comprising:
an elongated housing member extending along a longitudinal axis from a handle at a proximal end to an opening at a distal end, the housing member defining an internal bore extending axially along the longitudinal axis from the opening to the handle, the internal bore comprising a pair of guide pins disposed transversely to the longitudinal axis proximally to the opening;
a dispensing member defining an interior magazine area structured to hold a plurality of implants at a proximal end and a pair of flexible implant engaging arms further defining an implant gripping portion at a distal end;
at least two implant retaining members pivotally coupled to the housing member adjacent the opening at the distal end of the housing member; and
wherein the dispensing member is longitudinally translatable within the internal bore of the housing member such that when the dispensing member is moved toward the opening of the housing member the guide pins contact the implant engaging arms to stop translational movement at a first position where the implant engaging arms are positioned to engage a first implant therebetween with the implant gripping portion and when the dispensing member is moved away from the opening of the housing member the guide pins contact the implant engaging arms to stop translational movement at a second position where the implant engaging arms are spaced apart to release the first implant and form a passageway for a second implant to be delivered from the magazine area to the implant gripping portion while the retaining members are biased toward the opening of the housing member to prevent the second implant from exiting through the opening of the housing portion.

19. The surgical instrument of claim 18, wherein the implant engaging arms are disposed opposite each other and the implant retaining members are disposed opposite each other, such that the implant engaging arms and implant retaining members are situated generally around the surgical instrument.

20. The surgical instrument of claim 18, wherein the implant retaining members are spring-loadedly coupled about the opening at the distal end of the housing member.

21. The surgical instrument of claim 18, wherein each of the implant engaging arms defines a groove area adjacent to the implant gripping portion, the grooves being tapered distally and engaged with the guide pins.

22. The surgical instrument of claim 18, wherein the implant gripping portion of the implant engaging arms is structured to grip a respective one of the implants during rotational insertion of the respective implant into an implantable receiving member when the dispensing member is at the first position.

23. The surgical instrument of claim 18, wherein the dispensing member includes a spring biased pushing member structured to distally advance the plurality of implants toward the implant gripping portion of the implant engaging arms when the dispensing member is at the second position.

24. A surgical system, comprising:
a receiving member implantable in a patient, the receiving member including at least one receptacle;
an instrument including a proximal handle member, a magazine member defining an implant magazine and a distal implant driver, a housing member coupled with the handle member and extending longitudinally about the magazine member with the magazine member being translatably positionable therein, and a pair of implant retaining members at a distal end of the housing member; and
a plurality of implants positioned within the implant magazine of the interior magazine member and movable therewithin toward the implant driver, the implant driver being structured to receive a first implant of the plurality of implants and the implant retaining members being structured to retain the first implant at the implant driver as the magazine member is translated within the housing member in a first longitudinal direction, the implant driver being further structured to tighten about the first implant in response to the magazine member translating within the housing member in a second longitudinal direction opposite the first direction, and wherein at least one of the implants is engageable in the at least one receptacle of the receiving member when delivered from the implant driver through a distal end opening of the housing member as the handle member is rotated to rotate the implant driver and the implant.

25. The surgical system of claim 24, wherein the retaining members are pivotally coupled to the housing member about the distal end opening.

26. The surgical system of claim 24, wherein the receiving member is engageable to a spinal column of the patient and the implants are externally threaded set screws threadingly engageable in the at least one receptacle.

27. The surgical system of claim 24, wherein the housing member further comprises a pair of guide members structured to direct the implant driver to tighten about the first implant as the magazine member is translated in the second direction.

* * * * *